US007105489B2

(12) United States Patent
Hathaway

(10) Patent No.: US 7,105,489 B2
(45) Date of Patent: Sep. 12, 2006

(54) METHODS AND COMPOSITIONS FOR TREATING POLYCYSTIC OVARY SYNDROME

(75) Inventor: David R. Hathaway, Lincoln, NE (US)

(73) Assignee: Amylin Pharmaceuticals, Inc., San Diego, CA (US)

(*) Notice: Subject to any disclaimer, the term of this patent is extended or adjusted under 35 U.S.C. 154(b) by 666 days.

(21) Appl. No.: 10/317,126

(22) Filed: Dec. 11, 2002

(65) Prior Publication Data

US 2004/0029784 A1 Feb. 12, 2004

Related U.S. Application Data

(60) Provisional application No. 60/350,395, filed on Jan. 22, 2002.

(51) Int. Cl.
*A61K 38/22* (2006.01)
(52) U.S. Cl. .......................................... 514/21; 514/12
(58) Field of Classification Search ................ None
See application file for complete search history.

(56) References Cited

U.S. PATENT DOCUMENTS 6,329,403 B1 12/2001 Odaka et al.
2004/0180824 A1 9/2004 Knudsen

OTHER PUBLICATIONS

Stephen Franks, M.D., "Polycystic Ovary Syndrome", *Medical Progress*, vol. 333, No. 13, p. 853-861, Reproductive Endocrinology Group, Department of Obstetrics and Gynecology, St. Mary's Hospital Medical School, Imperial College of Science, Technology and Medicine, University of London, London W2 IPG, United Kingdom (1995).
Robert L. Barbieri, MD, "Induction Of ovulation in Infertile Women With Hyperandrogenism And Insulin Resistance", *Am J. Obstet Gynecol*, 2000; 183:1412-8, Copyright 2002 by Mosby, Inc., From the Department of Obstetrics, *Gynecology* and Reproductive Biology, Brigham and Women's Hospital, Harvard Medical School, p. 1412-1418.
Laurence Udoff and Eli Y. Adashi, "Polycystic ovarian disease: a new look at an old subject", *Current Opinion in Obstetrics and Gynecology*, 1995, 7:340-343, Rapid Science Publishers ISSN 1040-872X, Division of Reproductive Endocrinology, Department of Obstetrics and Gynecology, University of Maryland School of Medicine, Baltimore, Maryland, USA.
Lena H. Kim, M.D., Ann E Taylor, M.D. and Robert L. Barbieri, M.D., *Fertility And Sterility*, vol. 73. No. 6, Jun. 2000, "Insulin sensitizers and polycystic ovary syndrome: can a diabetes medication treat infertility?", vol. 73, No. 6, Jun. 2000, Copyright 2000 American Society for Reproductive Medicine, Published by Rapid Science Printed USA, pp. 1097-1098.
Joffe Hadine, Ann E. Taylor and Janet E. Hall, "Editorial: Pelycystic Ovarian Syndrome—Relationship to Epilepsy and Antiepileptic Drug Therapy", *The Journal of Clincal Endocrinology & Metabolism*, Copyright 2001 by the Endocrine Society, vol. 86, No. 7, Women's Center for Behavioral Endocrinology, McLean Hospital (H.J.) Belmont, Mass, pp. 2946-2949.
Maria J. Iuorno, M.D. and John E. Nestler, M.D., *Obstetrics and Gynecology Clinics of North America*, "Insulin-Lowering Drugs in Polycystic Ovary Syndrome", vol. 28, No. 1, Mar. 2001, Department of Medicine, Division of Endocrinology and Metabolism, Virginia Commonwealth University, Medical College of Virginia, Richmond, VA., pp. 153-164.
Howard A. Zachur, "Polycystic Ovary Syndrome, Hyperandrogenism, and Insulin Resistance", *Obstetrics and Gynecology Clinics of North America*, vol. 28, No. 1, Mar. 2001, Department of Gynecology and Obstetrics, Division of Reproductive Endocrinology, The Johns Hopkins University School of Medicine, Baltimore, Maryland, pp. 21-33.
William R. Phipps, M.D., "Polycystic Ovary Syndrome and Ovulation Induction", *Obstetrics and Gynecology Clinics of North America*, vol. 28, No. 1, Mar. 2001, Department of Obstetrics and Gynecology, University of Rochester School of Medicine and Dentistry, Rochester, New York, pp. 165-182.
Lynda J. Wolf, M.D., "Ovulation Induction", *Clinical Obstetrics and Gynecology*, vol. 43, No. 4, pp. 902-915, Copyright 2000, Lippincott Williams & Wilkins, Inc.
Adam Balen, "Ovulation Induction for polycystic ovary syndrome", *Human Fertility*, 2000, 3, 106-111, Department of Reproductive Medicine, The General Infirmary, Copyright The British Fertility Society, Leeds LS2 9NS, UK, 1464-7273/2000.
Gerard S. Conway, "Hyperinsulinaemia and polycystic ovary syndrome", *Human Fertility* (2000) 3, 93-95, 2000 The British Fertility Society 1464-7273/2000.
Bridget Lieser Ahles, M.D., "Toward a New Approach: Primary and Preventive Care of the Woman With Polycystic Ovarian Syndrome", *Primary Care Update OB/Gyns 2000*; 7: 275-278, Copyright 2000 Elsevier Science, Inc. (PII S 1068-607X(00)00059-7.
Richard S. Legro, M.D., "Polycystic ovary syndrome: Current and future treatment", *Am J. Obstet Gynecol 1998*, 179:S101-8) Copyright 1998 by Mosby, Inc.
M. Ciampelli and A. Lanzone, "Insulin and polycystic ovary syndrome: a new look at an old subject", *Gynecol Endocrino* 1998; 12:277-292; Department of Obstetrics and Gynecology, Catholic University of Sacred Heart, Rome, Italy; and *OASI Institute for Research, Troina (EN), Italy.
Rina M. Davison, "New approaches to insulin resistance in polycystic ovarian syndrome", *Current Opinion in Obstetrics and Gynecology* 1998, 10:193-198; Division of Endocrinology, Department of Medicine, University College London, School of Medicine, The Middlesex Hospital, Mortimer Street, London W1N 8AA, UK; 1998 Lippincott-Raven Publishers.
Bruce M. Spiegelman, "PPARγ in Monocytes: Less Pain, Any Gain?", *Cell*, vol. 93, 153-155, Apr. 17, 1998, Copyright 1998 by Cell Press.
Jerrold M. Olefsky and Alan R. Saltiel, "PPARγ and the Treatment of Insulin Resistance", *TEM*, vol. 11, pp. 362-367, No. 9, 2000. 2000 Elsevier Science Ltd.
Michel Pugeat and Pierre Henri Ducluzeau, "Insulin Resistance, Polycystic Ovary Syndrome and Metformin", *Drugs*, 1999 58 Suppl. 1:41-46, Adis International Limited.

(Continued)

Primary Examiner—Jeffrey Edwin Russel

(57) ABSTRACT

The present invention relates to methods of treating polycystic ovary syndrome (PCOS) comprising administering glucagon-like peptide-1 (GLP-1) to subjects suffering therefrom.

20 Claims, No Drawings

OTHER PUBLICATIONS

Stephen Franks, M.D., FRCP, HON MD (Uppsala), Carole Gilling-Smith, PhD, MRCOG, Hazel Watson, BSc, MSc, and Debbie Willis, PhD, "Insulin Action in the Nomal and Polycystic Ovary", *Endocrinology And Metabolism Clinics Of North America*, vol. 28, No. 2, Jun. 1999, pp. 361-378, Department of Reproductive Science and Medicine, Imperial College School of Medicine, St. Mary's Hospital; and the Assisted Conception Unit, Chelsea & Westminster Hospital, London, UK.

Robert L. Rosenfield, M.D., "Current Concepts of Polycystic Ovary Syndrome", *Bailliere's clinical Obstetrics and Gynaecology*, vol. 11, No. 2, Jun. 1997, pp. 306-332, Copyright 1997, by Bailliere Tindall.

Zoe E. C Hopkinson, Naveed Sattar, Richard Fleming, Ian A Greer, "Polycystic ovarian syndrome: the metabolic syndrome comes to gynaecology", vol. 11, No. 2, Jun. 1997, pp. 329-332, *BMJ*, vol. 317, Aug. 1, 1998.

David A. Ehrmann, M.D., "Relation of functional ovarian Hyperandrogenism to non-insulin dependent diabetes mellitus", *Vailliere's Clinical Obstetrics and Gynaecology*, vol. 11, No. 2, Jun. 1997, 335-346; Copyright 1997 by Bailliere Tindall.

John E. Nestler, M.D., "Role of Hyperinsulinemia in the Patho9genesis of the Polycystic Ovary Syndrome, and Its Clinical Implications", *Seminars in Reproductive Endocrinology*, vol. 15, No. 2, May 1997, pp. 111-122, Copyright 1997 by Thieme Medical Publishers, Inc.

Robert D. Utiger, M.D., *The New England Journal of Medicine*, pp. 657-658, Aug. 29, 1996, 1996 Massachusetts Medical Society.

SEQUENCE LISTING

```
<160> NUMBER OF SEQ ID NOS: 13

<210> SEQ ID NO 1
<211> LENGTH: 37
<212> TYPE: PRT
<213> ORGANISM: Mammalian

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: Mammalian
<220> FEATURE:
<221> NAME/KEY: MOD_RES
<222> LOCATION: (36)..(36)
<223> OTHER INFORMATION: AMIDATION

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 3
<211> LENGTH: 31
<212> TYPE: PRT
<213> ORGANISM: Mammalian

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Mammalian
```

```
<220> FEATURE:
<221> NAME/KEY: MOD_RES
<222> LOCATION: (30)..(30)
<223> OTHER INFORMATION: AMIDATION

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 29
<212> TYPE: PRT
<213> ORGANISM: Mammalian

<400> SEQUENCE: 5

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: Mammalian
<220> FEATURE:
<221> NAME/KEY: MOD_RES
<222> LOCATION: (28)..(28)
<223> OTHER INFORMATION: AMIDATION

<400> SEQUENCE: 6

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: AMIDATION

<400> SEQUENCE: 7

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 8
<211> LENGTH: 31
<212> TYPE: PRT
<213> ORGANISM: Heloderma suspectum
<220> FEATURE:
<221> NAME/KEY: MOD_RES
<222> LOCATION: (31)..(31)
<223> OTHER INFORMATION: AMIDATION
```

```
<400> SEQUENCE: 8

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 9
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: AMIDATION

<400> SEQUENCE: 9

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Heloderma suspectum

<400> SEQUENCE: 10

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 11
<211> LENGTH: 37
<212> TYPE: PRT
<213> ORGANISM: Heloderma suspectum

<400> SEQUENCE: 11

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 12
<211> LENGTH: 35
<212> TYPE: PRT
<213> ORGANISM: Heloderma suspectum
<220> FEATURE:
<221> NAME/KEY: MOD_RES
<222> LOCATION: (35)..(35)
<223> OTHER INFORMATION: AMIDATION
```

-continued

```
<400> SEQUENCE: 12

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 13
<211> LENGTH: 35
<212> TYPE: PRT
<213> ORGANISM: Heloderma suspectum
<220> FEATURE:
<221> NAME/KEY: MOD_RES
<222> LOCATION: (35)..(35)
<223> OTHER INFORMATION: AMIDATION

<400> SEQUENCE: 13

His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35
```

METHODS AND COMPOSITIONS FOR TREATING POLYCYSTIC OVARY SYNDROME

CROSS REFERENCE TO RELATED APPLICATIONS

This application claims the benefit of priority of U.S. Provisional Application Ser. No. 60/350,395, filed Jan. 22, 2002.

FIELD OF THE INVENTION

The present invention relates to endocrinology and pharmacology. More particularly, it relates to methods and compositions for treating subjects suffering from polycystic ovary syndrome (PCOS).

BACKGROUND OF THE INVENTION

Polycystic ovary syndrome (PCOS), also known as polycystic ovarian disease or Stein-Leventhal syndrome, affects an estimated 6–10% of women in the United States. PCOS is characterized by anovulation (irregular or absent menstrual periods) and hyperandrogenism (elevated serum testosterone and androstenedione). Additional etiological and clinical symptoms of this disease can include abnormal uterine bleeding, enlarged multifollicular ovaries, infertility, obesity, insulin resistance, hyperinsulinemia, hypertension, hyperlipidemia, type-2 diabetes mellitus, excess facial hair growth, hair loss and acne.

Insulin resistance and hyperinsulinemia are highly prevalent in patients with PCOS and are thought to underlie the pathophysiology of this disease (Udoff, L., et al., *Curr. Opin. Obstret. Gynecol.* 7:340–343 (1995); Barbieri, R. L., *Am. J. Obstet. Gynecol.* 183:1412–8 (2000); Kim, L. H. et al., *Fertility and Sterility* 73:1097–1098 (2000); Iuorno, M. J. et al., *Obstet. Gynecol. Clin. North Am.* 28:153–164 (2001); Zacur, H. Z., *Obstet. Gynecol. Clin. North Am.* 28:21–33 (2001)). Recent studies suggest that the hyperandrogenism associated with PCOS is caused by an increase in ovarian androgen production (e.g., testosterone and androstenedione) and a decrease in serum androgen-binding globulin concentration, due to hyperinsulinemia. Insulin has been shown to directly stimulate production of androgens by the ovary, at least in part by increasing the activity of P450c17α, an enzyme involved in the production of testosterone in the ovarian theca cells (Iuorno, M. J. et al., supra). At the level of the pituitary axis, hyperandrogenism suppresses follicle stimulating hormone (FSH) secretion, alters gonadotropin-releasing hormone (GnRH) release and increases lutenizing hormone (LH) secretion. These abnormalities, along with the local effects of androgens on the ovaries, lead to follicular involution, anovulation, and infertility. Similarly, oligomenorrhea and amenorrhea occur and are interspersed with heavy vaginal bleeding. Hyperinsulinemia may also lead to high blood pressure and increased clot formation and has been implicated in the development of cardiovascular disease, stroke and type-2 diabetes (Iuorno, M. J. et al., supra; Zacur, H. A., supra).

Traditionally, treatment of PCOS was directed primarily at correcting the underlying symptoms. For example, hirsutism and menstrual irregularities were treated with anti-androgenic drugs, including birth control pills, spironolactone, flutamide or finasteride. Infertility treatments have included weight loss diets, ovulation medications (e.g., clomiphene, follistim and Gonal-F), so-called "ovarian drilling" surgery, and in vitro fertilization. More recent treatments for PCOS are targeted towards lowering insulin levels. Insulin-sensitizing agents such as metformin, D-Chiro-inositol, diazoxide, and PPAR-gamma inhibitors (e.g., troglitazone (Rezulin), rosiglitazone (Avandia) and pioglitazone (Actos)), have been demonstrated to restore fertility and reverse the endocrine abnormalities associated with PCOS. Although metformin and PPAR-gamma inhibitors do not interfere with pregnancy, they are generally discontinued during pregnancy because of concern over their safety and effect(s) on the fetus. Moreover, women with PCOS who become pregnant experience spontaneous abortion during the first trimester at rates as high as 30% to 50% (Iuorno, M. J. et al., supra; Zacur, H. A., supra; Phipps, W. R., *Obstet. Gynecol. Clin. North Am.* 28:165–182 (2001). Thus, there is a need for new and better compositions and methods for treating PCOS.

SUMMARY OF THE INVENTION

Applicants have solved the above problem by discovering that glucagon-like peptide-1 (GLP-1) is capable of lowering insulin resistance or increasing insulin sensitivity. The present invention relates to methods for treating PCOS using GLP-1. In one embodiment, the methods of this invention comprise administering to a patient a therapeutically effective amount of GLP-1. In another embodiment, the method comprises reducing or preventing insulin resistance in a subject suffering from PCOS. In yet another embodiment, the method comprises preventing the onset of type-2 diabetes in a subject suffering from PCOS. In a further embodiment, the method comprises restoring regular menses, ovulation, or fertility in a subject suffering from PCOS.

In a preferred embodiment, the GLP-1 molecule is selected from the groups consisting of GLP-1(7–36)NH$_2$, GLP-1(7–37), and exendin-4. In another preferred embodiment, the subject is human.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application, including the definitions, will control. All publications, patents and other references mentioned herein are incorporated by reference.

Although methods and materials similar or equivalent to those described herein can be used in the practice of the present invention, suitable methods and materials are described below. The materials, methods, and examples are for illustrative purposes only, and are not intended to be limiting. Other features and advantages of the invention will be apparent from the detailed description and from the claims.

Throughout this specification, the word "comprise" or variations such as "comprises" or "comprising" will be understood to imply the inclusion of a stated integer or groups of integers but not the exclusion of any other integer or group of integers.

In order to further define the invention, the following terms and definitions are herein provided.

The term "alopecia" as used herein, refers to a condition in which a patient experiences loss of hair due to, e.g., infections of the scalp or skin, nervousness, or a specific disease such as PCOS. The hair may fall out in patches or there may be diffuse loss of hair instead of complete baldness in one area.

The terms "GLP-1," "GLP-1 molecule," "glucagon-like peptide-1," or "glucagon-like peptide-1 molecule" according to this invention include GLP-1 and biologically active variants, analogs, mimetics, agonists, and derivatives thereof, including exendin-4. "Biologically active" in this context means having the biological activity of GLP-1 (7–36)amide (GLP-1(7–36)$NH_2$), but it is understood that the activity of the variant, analog, mimetic, agonist, or derivative can be either less potent or more potent than native GLP-1(7–36)amide. The agonists of GLP-1 a GLP-1 mimetics that function as agonists include, e.g., chemical compounds specifically designed to activate the GLP-1 receptor.

The term "hirsutism" as used herein, refers to a condition in which a patient exhibits abnormal hairiness.

The term "hyperandrogenism" as used herein, refers to a condition in which a patient exhibits elevated levels of androgens (e.g., testosterone, androstenedione) in serum.

The term "hyperinsulinemia" as used herein, refers to a condition in which a patient exhibits elevated plasma insulin levels.

The term "hyperlipidemia" as used herein, refers to a condition in which a patient exhibits elevated concentrations of any or all lipids in plasma.

The term "hypertension" as used herein, refers to a condition in which a patient experiences persistently high blood pressure (i.e., a systolic pressure equal or greater than 140 mm Hg and a diastolic pressure equal to or greater than 90 mm Hg).

The term "insulinotropic" as used herein, refers to an ability to stimulate the release of insulin into the circulation.

The term "insulin resistance" as used herein, describes a subnormal biological response to a given concentration of insulin (i.e., decreased glucose transport across the cell membrane in response to insulin).

The term "pharmaceutically acceptable carrier or adjuvant" as used herein, refers to a non-toxic carrier or adjuvant that may be administered to a patient together with a compound of the invention, and which does not destroy the pharmacological activity thereof.

The terms "polycystic ovarian syndrome," "PCOS," "polycystic ovarian disease" or "Stein-Leventhal syndrome" as used herein refer to a disease affecting women. Women diagnosed with PCOS may exhibit one or more of the following symptoms: anovulation (irregular or absent menstrual periods), hyperandrogenism (elevated serum testosterone and/or androstenedione), abnormal uterine bleeding, enlarged multifollicular ovaries, infertility, obesity, insulin resistance, hyperinsulinemia, hypertension, hyperlipidemia, type-2 diabetes mellitus, excess facial hair growth, hair loss, and acne.

The terms "therapeutically or pharmaceutically effective" or "therapeutically or pharmaceutically effective amount" refers to an amount of the compound of this invention required to reduce or lessen the severity of PCOS or any of its symptoms (e.g., of insulin resistance, hyperinsulinemia, type-2 diabetes mellitus, obesity, hypertension, hyperlipidemia, anovulation or irregular ovulation, infertility, hyperandrogenism, hirsutism, alopecia, acne, enlarged multifollicular ovaries and abnormal uterine bleeding, for some period of time). A therapeutically or pharmaceutically effective amount also means the amount required to improve the clinical symptoms of a patient.

The term "type-2 diabetes mellitus" as used herein, refers to a disease, also known as non-insulin-dependent diabetes mellitus (NIDDM) or adult-onset diabetes mellitus (AODM), in which a patient has elevated concentrations of blood sugar levels.

The present invention relates to methods for treating PCOS in a patient. The methods include administering to a subject a therapeutically effective amount of GLP-1. The methods of this invention further relate to lowering insulin resistance using GLP-1. Many of the symptoms associated with PCOS stem from an underlying insulin resistance.

Glucagon-Like Peptide-1 (GLP-1)

GLP-1 plays a key role in the regulation of plasma glucose homeostasis. It is involved in stimulating insulin secretion and inhibiting glucagon release by the pancreas, inhibiting gastric acid secretion and motility, and suppressing appetite and food intake. GLP-1 is a member of the incretin group of secretagogue hormones that are released from intestinal enteroendocrine cells in response to the ingestion of food. GLP-1 binds to the GLP-1 receptor, which is expressed on the β-cells of the pancreas. Binding of GLP-1 to its receptor triggers an intracellular signaling pathway that results in stimulation of insulin secretion with concomitant inhibition of glucagon production. This in turn leads to inhibition of hepatic glucose production, which lowers blood glucose levels. Although the role of GLP-1 in maintaining plasma glucose concentration is well established, prior to this invention, it was not known that GLP-1 is also capable of increasing insulin sensitivity.

As used herein, a "GLP-1 molecule" includes the following compounds. Mammalian GLP peptides and glucagon are encoded by the same gene. In the ileum, the precursor is processed into two major classes of GLP peptide hormones, namely GLP-1 and GLP-2. GLP-1(1–37) has the sequence: His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 1). GLP-1(1–37) is amidated post-translationally to yield GLP-1(1–36)$NH_2$, which has the sequence: His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg($NH_2$) (SEQ ID NO: 2), or is enzymatically processed to yield GLP-1(7–37), which has the sequence: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 3). GLP-1(7–37) can also be amidated to yield GLP-1(7–36) amide, which has the sequence: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg($NH_2$) (SEQ ID NO: 4). Likewise, GLP-1(1–36)amide can be processed to GLP-1(7–36)amide.

Intestinal L cells secrete GLP-1(7–37) (SEQ ID NO: 3) and GLP-1(7–36)$NH_2$ (SEQ ID NO: 4) in a ratio of about 1:5. These truncated forms of GLP-1 have short half-lives in vivo (less than 10 minutes), and are inactivated by an aminodipeptidase (DPP IV) to yield GLP-1(9–37), which has the sequence: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NQ: 5), and GLP-1(9–36)amide, which has the sequence: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg($NH_2$) (SEQ ID NO: 6), respectively. It has been speculated that the peptides GLP-1(9–37) and GLP-1(9–36)amide might affect hepatic glucose production, but apparently they do not stimulate production or release of insulin from the pancreas.

As used in this specification, the term "GLP-1 molecule" includes GLP-1(1–37), GLP-1(1–36)NH$_2$, GLP-1(7–37), GLP-1(7–36)NH$_2$ ("GLP-1(7–36)amide"), GLP-1(9–37), GLP-1(9–36)NH$_2$ ("GLP-1(9–36)amide") (collectively referred to as "GLP-1 peptides"). The present invention includes the use of recombinant human GLP-1 peptides and GLP-1 peptides derived from other species, whether recombinant or synthetic.

"GLP-1 molecule" further denotes biologically active variants, analogs, and derivatives of GLP-1 peptides. "Biologically active," in this context, means having GLP-1 (7–36) biological activity, but it is understood that the variant, analog, or derivative can be either less or more potent than GLP-1(7–36)amide, a native, biologically active form of GLP-1. See Goke & Byrne, *Diabetic Medicine*. 13; 854 (1996). GLP-1 molecules of the present invention also include polynucleotides that express agonists of GLP-1 (i.e., activators of the GLP-1 receptor molecule and its secondary messenger activity found on, inter alia, insulin-producing β-cells). GLP-1 mimetics that also are agonists of GLP-1 receptors include, for example, chemical compounds specifically designed to activate the GLP-1 receptor.

Included in GLP-1 molecules are any molecules, whether they be peptides, peptide mimetics, or other molecules, that bind to or activate a GLP-1 receptor, such as the GLP-1 (7–36)amide receptor, and its second messenger cascade. GLP-1 molecules include species having insulinotropic activity and that are agonists of (i.e., activate) the GLP-1 receptor molecule and its second messenger activity on, inter alia, insulin producing β-cells.

"GLP-1 molecules" also include peptides that are encoded by polynucleotides that express biologically active GLP-1 variants, as defined herein. Also included in the present invention are GLP-1 molecules that are peptides containing one or more amino acid substitutions, additions or deletions, compared with GLP-1(7–36)amide. In one embodiment, the number of substitutions, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. A "conservative" substitution denotes the replacement of an amino acid residue by another, biologically active similar residue. Examples of conservative substitutions include the substitution of one hydrophobic residue, such as isoleucine, valine, leucine, or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

| ORIGINAL RESIDUE | EXEMPLARY SUBSTITUTIONS |
| --- | --- |
| ALA | SER, THR |
| ARG | LYS |
| ASN | HIS, SER |
| ASP | GLU, ASN |
| CYS | SER |
| GLN | ASN, HIS |
| GLU | ASP, GLU |
| GLY | ALA, SER |
| HIS | ASN, GLN |
| ILE | LEU, VAL, THR |

-continued

| ORIGINAL RESIDUE | EXEMPLARY SUBSTITUTIONS |
| --- | --- |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that GLP-1 peptide variants include the above described peptides which have been chemically derivatized or altered, for example, peptides with non-natural amino acid residues (e.g., taurine, β- and γ-amino acid residues and D-amino acid residues), C-terminal functional group modifications, such as amides, esters, and C-terminal ketone modifications and N-terminal functional group modifications, such as acylated amines, Schiff bases, or cyclization, as found-for example-in the amino acid pyroglutamic acid.

Also included in the present invention are peptide sequences having greater than 50% sequence identity, and preferably greater than 90% sequence identity to (1) SEQ ID NOS: 1, 2, 3, 4; and (2) to truncated sequences thereof. As used herein, sequence identity refers to a comparison made between two molecules using standard algorithms well known in the art. The preferred algorithm for calculating sequence identity for the present invention is the Smith-Waterman algorithm, where SEQ ID NO: 1 [i.e., GLP-1 (1–37)] is used as the reference sequence to define the percentage identity of homologs over its length. The choice of parameter values for matches, mismatches, and insertions or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and $-\frac{1}{3}$ for a mismatched residue (a residue being either a single nucleotide or single amino acid). Waterman, *Bull. Math. Biol.* 46; 473 (1984). Insertions and deletions (indels), x, are weighted as $x_k=1+\frac{1}{3}k$, where k is the number of residues in a given insert or deletion. Id.

For instance, a sequence that is identical to the 37-amino acid residue sequence of SEQ ID NO: 1, except for 18 amino acid substitutions and an insertion of 3 amino acids, would have a percent identity given by:

$$[(1\times 37 \text{ matches}) - (\tfrac{1}{3} \times 18 \text{ mismatches}) - (1+3/3 \text{ indels})]/37 = 78\% \text{ 'identity'}$$

Also included in "GLP-1 molecules" of the present invention are six peptides in Gila monster venoms that are homologous to GLP-1. Their sequences are compared to the sequence of GLP-1 in Table 1.

TABLE 1

```
a.  H A E G T F T S D V S S Y L E G Q A A K E F I A W L V K G R (NH₂)

b.  H S D G T F T S D L S K Q M E E E A V R L F I E W L K N G G P S S G A P P P S (NH₂)

c.          D L S K Q M E E E A V R L F I E W L K N G G P S S G A P P P S (NH₂)

d.  H G E G T F T S D L S K Q M E E E A V R L F I E W L K N G G P S S G A P P P S (NH₂)

e.  H S D A T F T A E Y S K L L A K L A L Q K Y L E S I L G S S T S P R P P S S f.  H S D A T F T A E Y S K L L A K L A L Q K Y L E S I L G S S T S P R P P S g.  H S D A I F T E E Y S K L L A K L A L Q K Y L A S I L G S R T S P P P (NH₂)

h.  H S D A I F T Q Q Y S K L L A K L A L Q K Y L A S I L G S R T S P P P (NH₂)
``` a= GLP-1(7–36)amide (SEQ. ID NO: 4)
b= exendin 3 (SEQ. ID NO: 7).
c= exendin 4 (9–39(NH2) (SEQ. ID NO: 8).
d= exendin 4 (SEQ. ID NO: 9).
e= helospectin I (SEQ. ID NO: 10).
f= helospectin II (SEQ. ID NO: 11)
g= helodermin (SEQ. ID NO: 12).
h= $Q^8$, $Q^9$ helodermnin (SEQ. ID NO: 13).

Peptides (a, b, d, e, f, and g) are homologous at positions 1, 7, 11 and 18. GLP-1 and exendins are further homologous at positions, 4, 5, 6, 8, 9, 15, 22, 23, 25, 26 and 29. In position 2, A (Ala), S (Ser), and G (Gly) are structurally similar. In position 3, residues D (Asp) and E (Glu) are structurally similar. In positions 22 and 23, F (Phe) and I (Ile) are structurally similar to Y (Tyr) and L (Leu), respectively. Likewise, in position 26, L and I are structurally similar.

Thus, of the 30 residues of GLP-1, exendins 3 and 4 are identical in 15 positions and equivalent in 5 additional positions. The only positions where major structural changes are evident are at residues 16, 17, 19, 21, 24, 27, 28 and 30. Exendins also have 9 extra residues at the C-terminus.

Agonists of glucagon-like peptide that exhibit activity through the GLP-1(7–36)amide receptor have been described. See EP 0708179 A2; Hjorth et al., *J. Biol. Chem.* 269; 30121 (1994); Siegel et al., Amer. Diabetes Assoc. 57th Scientific Session, Boston (1997); Hareter et al., Amer. Diabetes Assoc. 57th Scientific Session, Boston (1997); Adelhorst et al., *J. Biol. Chem.* 269, 6275 (1994); Deacon et al., 16th International Diabetes Federation Congress Abstracts, *Diabetologia Supplement* (1997); Irwin et al., *Proc. Natl. Acad. Sci. USA* 94; 7915 (1997); Mojsov, *Int. J. Peptide Protein Res.* 40; 333 (1992). Göke & Byrne, *Diabetic Medicine* 13; 854 (1996). Recent publications disclose Black Widow GLP-1 and Ser² GLP-1. See Holz & Hakner, *Comp. Biochem. Physiol.*, Part B 121; 177 (1998) and Ritzel et al., *J. Endocrinol* 159; 93 (1998).

GLP-1 receptors are cell-surface proteins found, for example, on insulin-producing pancreatic β-cells; the GLP-1(7–36) receptor has been characterised in the art. Methods of determining whether a chemical or peptide binds to or activates a GLP-1 receptor are known to the skilled artisan.

The biological activity of a GLP-1 molecule can be determined by in vitro and in vivo animal models and human studies, as is well known to the skilled artisan. GLP-1 biological activity can be determined by standard methods, in general, by receptor binding activity screening procedures, which involve providing appropriate cells that express the GLP-1 receptor on their surface, for example, insulinoma cell lines such as RINmSF cells or INS-1 cells. See Mojsov, *Int. J. Peptide Protein Res.* 40; 333 (1992) and EP 0708179 A2. Cells that are engineered to express a GLP-1 receptor also can be used. In addition to measuring specific binding of tracer to membrane using radioimmunoassay methods, cAMP activity or glucose dependent insulin production can also be measured. In one method, a polynucleotide encoding the GLP-1 receptor is employed to transfect cells so that they express the GLP-1 receptor protein. Thus, for example, these methods may be employed for screening for a receptor agonist by contacting such cells with compounds to be screened and determining whether such compounds generate a signal (i.e., activate the receptor). Other screening techniques include the use of cells that express the GLP-1 receptor, for example, transfected CHO cells, in a system to measure extracellular pH or ionic changes caused by receptor activation. For example, potential agonists may be contacted with a cell that expresses the GLP-1 protein receptor and a second messenger response (e.g., signal transduction or ionic or pH changes), may be measured to determine whether the potential agonist is effective.

Polyclonal and monoclonal antibodies can be utilized to detect, purify, and identify GLP-1-like peptides for use in the methods described herein. Antibodies such as ABGA1178 detect intact GLP-1(1–37) or N-terminally-truncated GLP-1(7–37) or GLP-1(7–36)amide. Other antibodies detect the end of the C-terminus of the precursor molecule, a procedure that allows one-by subtraction-to calculate the amount of biologically active, truncated peptide (i.e., GLP-1(7–37) amide). Orskov et al., *Diabetes* 42; 658 (1993); Orskov et al., *J. Clin. Invest.* 1991, 87; 415 (1991).

The GLP-1 molecules of the invention that are peptides that can be made by solid-state chemical peptide synthesis. Such peptides can also be made by conventional recombinant techniques using standard procedures described in, for example, Sambrook & Maniatis, Molecular Cloning, A Laboratory Manual. "Recombinant," as used herein, means that a gene is derived from a recombinant (e.g., microbial or mammalian) expression system that has been genetically modified to contain a polynucleotide encoding a GLP-1 molecule as described herein.

The GLP-1 molecule peptides of the present invention may be a naturally purified product, or a product of synthetic chemical procedures, or produced by recombinant techniques from prokaryotic or eukaryotic hosts (for example, by bacteria, yeast, higher plant, insect, or mammalian cells in culture or in vivo). Depending on the host employed in a recombinant production procedure, the polypeptides of the present invention are generally non-glycosylated, but may be glycosylated.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High-performance liquid chromatography (HPLC) can be employed for final purification steps.

Particularly preferred GLP-1 molecules of the invention are GLP-1(7–36)amide, GLP-1(7–37), and exendin-4.

Uses for GLP-1

The methods and compositions of this invention may be used to treat PCOS. Many of the symptoms associated with PCOS stem from an underlying insulin resistance. The symptoms associated with PCOS include insulin resistance, hyperinsulinemia, hyperandrogenism, type-2 diabetes mellitus, irregular menses, anovulation and infertility. Therefore, the present invention provides methods of treating insulin resistance in a subject suffering from PCOS comprising the step of administering GLP-1.

Insulin resistance may be due to any one or more events including abnormal prereceptor (e.g., abnormal ligand or competition), receptor (e.g., abnormal structure, affinity of ligand to receptor, or number of receptors), or postreceptor (e.g., abnormal signaling) events. Insulin resistance may be determined by a number of methods known in the art. For example, the euglycemic hyperinsulinemic clamp technique may be used to diagnose insulin resistance (Rao, G., *Am. Fam. Physician* (2001) 63:1159–63). This technique involves intravenous administration of an insulin dose while simultaneously maintaining glucose at a pre-set level within the normal range by also administering glucose. At equilibrium, the amount of glucose uptake by a particular tissue in the presence of a certain dose of insulin can be calculated. Other methods used to detect insulin resistance include the insulin suppression test, intravenous glucose tolerance test, and constant infusion of glucose with model assessment (Rao, G., supra).

In another embodiment, the invention provides a method of preventing the onset of type-2 diabetes mellitus in a subject suffering from PCOS comprising the step of administering GLP-1. Type-2 diabetes mellitus is often a result of hyperinsulinemia caused by insulin resistance. Thus, treating insulin resistance in these patients would prevent the development of type-2 diabetes mellitus. Methods of diagnosing type-2 diabetes mellitus are well-known in the art.

In yet another embodiment, this invention provides a method of restoring regular menses, restoring regular ovulation and/or restoring fertility in a subject suffering from PCOS comprising the step of administering GLP-1. PCOS patients often exhibit hyperandrogenism, which is thought to be caused by hyperinsulinemia. The hyperandrogenism leads to follicular involution, anovulation and infertility. Thus, reducing insulin resistance by administering a GLP-1 molecule can ameliorate hyperinsulinemia, thereby restoring regular menses, ovulation, and/or fertility.

In another embodiment, this invention provides a method for treating PCOS comprising coadministering to a patient in need thereof GLP-1 with a drug that induces ovulation (e.g., clomiphene, follistim, or Gonal-F).

In yet another embodiment, this invention provides a method for treating PCOS comprising coadministering to a patient in need thereof GLP-1 with an anti-androgenic drug, including but not limited to a birth control pill (e.g., progestogens and estrogens), spironolactone, flutamide and finasteride.

In yet another embodiment, this invention provides a method for treating PCOS comprising coadministering to a patient in need thereof GLP-1 with an insulin-sensitizing agent, including, but not limited to, metformin, D-Chiro-inositol, diazoxide, and PPAR inhibitors (e.g., troglitazone (Rezulin), rosiglitazone (Avandia) and pioglitazone (Actos)).

In another embodiment, this invention provides a method for treating PCOS comprising coadministering to a patient in need thereof GLP-1 with glucose. In a more preferred embodiment the glucose is administered intravenously.

When the compounds of this invention are administered in combination therapies as described above, they may be administered sequentially or concurrently to the patient. Alternatively, the pharmaceutical compositions of this invention may be comprised of a combination of a GLP-1 molecule and another agent as described above.

In a preferred embodiment, the subject suffering from PCOS is a mammal, e.g., dog, cat, rodent. In a more preferred embodiment, the subject suffering from PCOS is a human.

Pharmaceutical Compositions

The GLP-1 molecules may be formulated into pharmaceutical compositions for administration to subjects, including humans. These pharmaceutical compositions, preferably include an amount of GLP-1 effective to treat, e.g., insulin resistance, prevent the onset of type-2 diabetes mellitus, restore regular menses and/or ovulation and treat infertility in a subject suffering from PCOS, and a pharmaceutically acceptable carrier.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered by an infusion pump or subcutaneous injection of a slow release formulation Sterile injectable forms of the compositions of this invention may be aqueous or oleaginous suspension. These suspensions may be formulated according to techniques known in the art, using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms, including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions of this invention may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

For ophthalmic use, the pharmaceutical compositions may be formulated as micronized suspensions in isotonic, pH-adjusted sterile saline, or, preferably, as solutions in isotonic, pH-adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of GLP-1 molecule that may be combined with the carrier materials to produce a single dosage form will vary depending upon the host treated and the particular mode of administration. The compositions can be formulated so that a dosage of between 0.1–1000 pmoles/kg body weight/minute (when administered by infusion) of GLP-1 molecule is administered to a patient receiving these compositions. In some embodiments of the invention, the dosage is 1–10 pmoles/kg body weight/minute (when administered by infusion). In a preferred embodiment the dosage is 0.5–2.0 pmoles/kg/min when administered by intravenous infusion. The composition may be administered as a single dose, multiple doses, or over an established period of time in an infusion.

In a preferred embodiment, GLP-1 is administered to patients with confirmed polycystic ovary syndrome. In another preferred embodiment, GLP-1 is administered by injection at least once a day or by continuous infusion via pump. In yet another preferred embodiment, GLP-1 is formulated for administration from a subcutaneous depot over a period of days to weeks, oral administration or by intermittent inhalation.

A specific dosage and treatment regimen for any particular patient will depend upon a variety of factors, including the particular GLP-1 molecule, the patient's age, body weight, general health, gender, and diet, and the time of administration, rate of excretion, drug combination, and the severity of the particular disease being treated. Judgment of such factors by medical caregivers is within ordinary skill in the art. The amount of GLP-1 molecules will also depend on the individual patient to be treated, the route of administration, the type of formulation, the characteristics of the compound used, the severity of the disease, and the desired effect. The amounts of GLP-1 molecules can be determined by pharmacological and pharmacokinetic principles well-known in the art.

In order that the invention described herein may be more fully understood, the following examples are set forth. It should be understood that these examples are for illustrative purposes only and are not to be construed as limiting this invention in any manner.

EXAMPLES

1. Treatment of a PCOS Patient with GLP-1

Patients with PCOS are exclusively women. Typically, premenopausal women manifest the disease with complaints of irregular menses, infertility, excessive growth of body hair, acne and loss of scalp hair. Postmenopausal women may have all of these complaints except irregular menses. Obesity, hypertension and diabetes are disorders that commonly accompany PCOS.

The diagnosis of PCOS will be confirmed by measuring the level of serum testosterone and/or the ratio of serum LH/FSH. Elevated levels of serum testosterone (>60 ng/ml) or an abnormal serum LH/FSH ratio (<2.5) are indicative of PCOS.

Patients with confirmed PCOS will be treated with GLP-1. GLP-1 will be administered by injection once or more each day or by continuous infusion via pump, which delivers a steady amount of drug. Alternatively, GLP-1 will be formulated for administration from a subcutaneous depot over days to weeks, by intermittent inhalation or orally.

Irrespective of the mode of administration, the total amount of GLP-1 delivered into the blood of a patient with PCOS will be in the range of 720 to 2880 picomoles/kg/day. This is equivalent to 0.5–2.0 pmoles/kg/min when administered by intravenous infusion.

The efficacy of GLP-1 will be established by determining the amelioration or reversal of the presenting complaint, including but not limited to normalization of menses, restoration of fertility, loss of excess body hair, resolution of acne and cessation of hair loss. Other indicators of GLP-1 efficacy may be used including but not limited to serum testosterone levels and LH/FSH ratios. GLP-1 efficacy will be determined by a decrease in serum testosterone levels and an increase in the LH/FSH ratio.

The invention claimed is:

1. A method of treating a subject suffering from polycystic ovary syndrome (PCOS) comprising the step of administering to a subject suffering from PCOS an amount of a GLP-1 molecule effective to treat at least one symptom of PCOS.

2. The method according to claim 1, wherein the symptom is selected from the group consisting of insulin resistance, hyperinsulinemia, type-2 diabetes, obesity, hypertension, hyperlipidemia, anovulation or irregular ovulation, infertility, hyperandrogenism, hirsutism, alopecia, acne, enlarged multifollicular ovaries; abnormal uterine bleeding, and spontaneous abortion.

3. A method of reducing insulin resistance in a subject suffering from PCOS comprising the step of administering to a subject suffering from PCOS an amount of a GLP-1 molecule effective to reduce insulin resistance, wherein said insulin resistance is a symptom of PCOS.

4. A method of preventing the onset of type-2 diabetes in a subject suffering from PCOS comprising the step of administering to a subject suffering from PCOS an amount of a GLP-1 molecule effective to prevent the onset of type-2 diabetes, wherein said type-2 diabetes is a symptom of PCOS.

5. A method of restoring regular menses in a subject suffering from PCOS comprising the step of administering to a subject suffering from PCOS an amount of a GLP-1 molecule effective to restore regular menses, wherein irregular menses is a symptom of PCOS.

6. A method of restoring regular ovulation in a subject suffering from PCOS comprising the step of administering to a subject suffering from PCOS an amount of a GLP-1 molecule effective to restore regular ovulation, wherein anovulation or irregular ovulation is a symptom of PCOS.

7. A method of restoring fertility in a subject suffering from PCOS comprising the step of administering to a subject suffering from PCOS an amount of a GLP-1 molecule effective to restore fertility, wherein the infertility is a symptom of PCOS.

8. A method for preventing spontaneous abortion in a subject suffering from PCOS comprising the step of administering to a subject suffering from PCOS an amount of a GLP-1 molecule effective to prevent spontaneous abortion, wherein said spontaneous abortion is a symptom of PCOS.

9. The method according to any one of claims 1 to 8, wherein the subject is human.

10. The method according to any one of claims 1 to 8, wherein the GLP-1 molecule is selected from the group consisting of GLP-1(7–36)NH$_2$, GLP-1(7–37), and exendin-4.

11. The method according to any one of claims 1 to 8, wherein the GLP-1 molecule is selected from the group consisting of GLP-1(7–36)NH$_2$ and GLP-1(9–36)NH$_2$.

12. The method according to any one of claims 1 to 8 wherein the GLP-1 is coadministered by an infusion pump or by subcutaneous injection of a slow release formulation.

13. The method according to any one of claims 1 to 8 wherein the GLP-1 is coadministered with an agent selected from the group consisting of an ovulation inducing drug, an anti-androgenic drug, an insulin-sensitizing agent and glucose.

14. The method according to claim 13 wherein the ovulation inducing drug is selected from the group consisting of clomiphene, follistim, and Gonal-F.

15. The method according to claim 13 wherein the anti-androgenic drug is selected from the group consisting of a birth control pill, spironolactone, flutamide, and finasteride.

16. The method according to claim 13 wherein the insulin-sensitizing agent is selected from the group consisting of metformin, D-Chiro-inositol, diazoxide, and PPAR inhibitor.

17. The method according to claim 13, wherein the glucose is administered intravenously.

18. The method according to claim 13, wherein the GLP-1 and the agent are administered either sequentially or concurrently.

19. The method of claim 16, wherein said PPAR inhibitor is triglitazone, rosiglitazone, or pioglitazone.

20. The method according to any one of claims 1 to 8, wherein the GLP-1 molecule is exendin-4.

* * * * *

UNITED STATES PATENT AND TRADEMARK OFFICE
CERTIFICATE OF CORRECTION

PATENT NO. : 7,105,489 B2
APPLICATION NO. : 10/317126
DATED : September 12, 2006
INVENTOR(S) : Hathaway It is certified that error appears in the above-identified patent and that said Letters Patent is hereby corrected as shown below:

Column 19, Line 42, change "ovaries;" to --ovaries,--.

Column 20, Line 52, change "coadministered" to --administered--.

Signed and Sealed this

Fourth Day of November, 2008

JON W. DUDAS
*Director of the United States Patent and Trademark Office*